United States Patent
Church et al.

(10) Patent No.: US 8,132,915 B2
(45) Date of Patent: Mar. 13, 2012

(54) BINOCULAR INDIRECT OPHTHALMOSCOPE

(75) Inventors: Kelvyn Church, Woodcote (GB); Stephen Church, Farnborough (GB); James Robert Arnold Matthews, Bracknell (GB); Eugene R. Vanarsdale, Philadelphia, PA (US)

(73) Assignee: Keeler Limited (GB)

( * ) Notice: Subject to any disclaimer, the term of this patent is extended or adjusted under 35 U.S.C. 154(b) by 59 days.

(21) Appl. No.: 11/912,263

(22) PCT Filed: Feb. 14, 2007

(86) PCT No.: PCT/GB2007/000503
§ 371 (c)(1),
(2), (4) Date: Jul. 29, 2008

(87) PCT Pub. No.: WO2007/104914
PCT Pub. Date: Sep. 20, 2007

(65) Prior Publication Data
US 2009/0096989 A1    Apr. 16, 2009

Related U.S. Application Data

(60) Provisional application No. 60/782,083, filed on Mar. 14, 2006.

(51) Int. Cl.
*A61B 3/10* (2006.01)

(52) U.S. Cl. ........................... 351/221; 351/205

(58) Field of Classification Search .................. 351/221, 351/205
See application file for complete search history.

(56) References Cited

U.S. PATENT DOCUMENTS

| 4,684,227 | A |   | 8/1987 | Schmidt et al. |
| 5,223,863 | A |   | 6/1993 | Heine et al. |
| 5,394,201 | A | * | 2/1995 | Hauptli ..................... 351/221 |

FOREIGN PATENT DOCUMENTS

GB    2182164 A    5/1987

* cited by examiner

*Primary Examiner* — Ricky Mack
*Assistant Examiner* — Zachary Wilkes
(74) *Attorney, Agent, or Firm* — Barnes & Thornburg LLP

(57) ABSTRACT

A binocular indirect opthalmoscope has a light source for producing an illumination beam and an illumination mirror (7) for directing the illumination beam to an eye to be viewed. The opthalmoscope also has, viewing optics including left-hand and right-hand eyepieces (12,13) and an optical splitter (9,10) for directing light along left-hand and right-hand viewing paths to the two eyepieces. An aperture holder (20) is pivotally mounted in a frame (3,5,6) of the opthalmoscope and adjusts the size of the illumination beam, under the control of a manually rotatable control knob (24). The movement of the aperture holder is transmitted, by means of mechanical linkage, to a moveable carriage (15) on which is mounted both the optical splitter and the illumination mirror, so that when the user moves the control knob to adjust the size of the illumination beam the optical splitter and the illumination mirror are also adjusted in position with respect to the opthalmoscope frame.

16 Claims, 5 Drawing Sheets

BINOCULAR INDIRECT OPHTHALMOSCOPE

RELATED APPLICATION

This application is the national filing of International Application No. PCT/GB2007/000503 filed Feb. 14, 2007, claiming priority to U.S. Provisional Application No. 60/782,083, filed Mar. 14, 2006.

FIELD OF THE INVENTION

This invention relates to binocular indirect opthalmoscopes and in particular to head-mounted binocular opthalmoscopes.

BACKGROUND TO THE INVENTION

Indirect opthalmoscopy, in particular binocular indirect opthalmoscopy, is a procedure commonly used to examine the fundus of an eye. The technique involves using a hand-held condensing lens which is placed between the examiner or user and the patient. This lens produces an aerial image of the retina that is viewed through the observation system of the opthalmoscope. The lens images the exit point of the illumination system and entrance point of the observation system in the pupillary plane of the patent's eye, thus ensuring a wide field of retinal illumination together with a wide field of observation.

The indirect opthalmoscope housing comprises a light source from which a beam is projected towards the eye via a plane mirror, angled such that the light passes through the hand held condensing lens before entering the eye. The condensing lens brings the light to a focus in the pupillary plane of the eye being examined. As a result of this arrangement, the paths of the illuminating and observation beams can be separated as they pass through the pupil, thus making the system capable of producing a reflex free view of the retina.

The opthalmoscope typically utilises a headband that enables the device to be mounted on the examiner's head. It also includes viewing optics through which an examiner can obtain a binocular view of the image of the fundus. The two viewing axes and the illumination light path must be able to pass through the pupil without interference.

For maximum stereopsis, the right and left viewing axes must be separated as far as possible from each other. The illumination beam, which must be focussed in the pupillary plane, should be positioned as near as possible to the pupil margin. This enables the illumination and observation paths to be separated as they pass though the pupil, thus decentring and minimising reflections from the cornea and the crystalline lens. Dilating the patient's pupil by means of a drug facilitates this process, but this may not always be possible.

The diameter of the illumination light beam can be varied by using a range of different light stops. Generally, the larger the pupil, the larger the diameter that is used.

Earlier instruments had viewing optics, illumination mirror and light source acting independently from each other. In addition, a range of illumination patch sizes is available for the examiner to select. This meant that the examiner was faced with a series of adjustments to make to achieve optimum viewing through a specific pupil size.

U.S. Pat. No. 4,449,767 attempted to overcome this by having two viewing mirrors arranged on a wedge shaped platform which could be moved towards or away from the patient's eye. The illumination mirror was mounted separately.

Heine et al. in U.S. Pat. Nos. 4,684,227 and 5,223,863 have attempted to overcome this further by mounting two viewing mirrors and a tilting illumination mirror on a common platform that can be moved toward and away from the object being viewed. This adjusts the position of the viewing and illumination axes, but a further adjustment to select optimum beam size is still required.

Welch Allyn in U.S. Pat. No. 5,394,201 achieve a similar result by having a pivoting illumination mirror connected to reflecting mirrors in a sliding carriage so that the axis of the light beam and the axes of the viewing paths move closer together or apart as the carriage moves in one direction or the other.

In all the above quoted patents which link the separate viewing and illumination axes, a further adjustment to select optimum beam size is still required.

Accordingly it is desirable to provide an improved binocular opthalmoscope for indirect observation of the eye that is easier for the examiner or user to adjust for optimum use.

SUMMARY OF THE INVENTION

According to one aspect of the invention there is provided a binocular indirect opthalmoscope comprising illumination optics including an adjustment device for selectively altering the size of an illumination beam and a beam directing device for directing the illumination beam of selected size to an eye to be viewed, the opthalmoscope further comprising viewing optics including left-hand and right-hand viewing eyepieces, an optical splitter for directing light travelling along left and right viewing paths respectively through the two eyepieces, wherein the beam directing device and optical splitter are moveable with respect to a frame of the opthalmoscope respectively to alter the position of the illumination beam and the lateral separation of the viewing paths, characterised in that the adjustment device for selectively altering the size of the illumination beam, the optical splitter and the beam directing device are linked such that adjustment of the size of the illumination beam results in a corresponding adjustment in the beam directing device and the position of the optical splitter.

Preferably, the beam directing device comprises an illumination mirror, the optical splitter and the illumination mirror being mounted on a common carriage moveable with respect to the frame of the opthalmoscope in a direction towards and away from the eye.

The preferred binocular indirect opthalmoscope functions such that when the adjustment device is adjusted an enlargement in size of the illumination beam causes the carriage to move in a direction towards the eye to be viewed and a reduction of the size of the illumination beam causes the carriage to move in a direction away from the eye to be viewed.

The linkage is preferably a mechanical linkage but may alternatively be electrical, hydraulic, pneumatic, electronic or opto-electrical.

The adjustment device preferably includes a control knob, movement of which selectively alters the size of the illumination beam and simultaneously effects movement of the common carriage so as to move the beam directing device and the illumination mirror. Hence, adjustment of the single control knob automatically adjusts the optical splitter positions and the illumination mirror height, as well as altering the size of the illumination beam.

According to another aspect of the invention there is provided a binocular indirect opthalmoscope comprising a frame; a light source supported by the frame for producing an illumination beam; an adjustment device including an aperture holder moveable with respect to the frame for altering the size of the illumination beam and a manually operable control member for controlling movement of the aperture holder: an illumination mirror for directing the illumination beam of adjusted size to an eye to be viewed; viewing optics including left-hand and right-hand viewing eyepieces and an optical splitter for directing light travelling along left-hand and right-hand viewing paths respectively to the two eyepieces; and a carriage moveable with respect to the frame in a direction towards and away from the eye to be examined, wherein the illumination mirror and the optical splitter are mounted on a carriage and the adjustment device is linked to the carriage such that movement of the control member in a direction causing reduction in the size of the illumination beam necessarily causes movement of the carriage, and therefore of the illumination mirror and the beam splitter, in a direction away from the eye to be viewed, and movement of the control member in a direction causing enlargement of the size of the illumination beam necessarily causes movement of the carriage, and therefore of the illumination mirror and the beam splitter, in a direction towards the eye to be viewed.

BRIEF DESCRIPTION OF THE DRAWINGS

The invention will now be further described, by way of example, with reference to the accompanying drawings, in which.

DETAILED DESCRIPTION OF THE DRAWINGS

Figure 1:
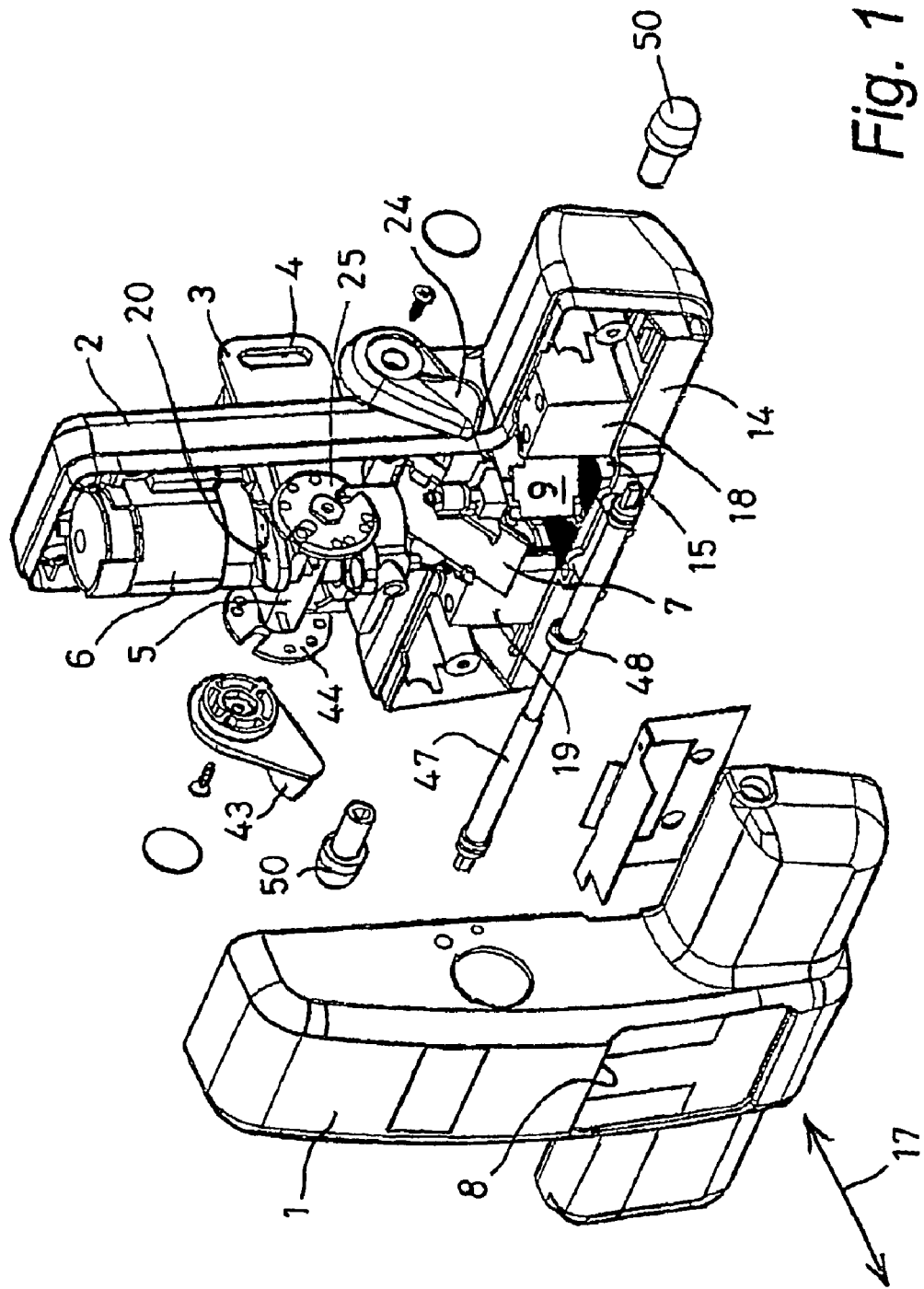
FIG. 1 is a view of a preferred embodiment of binocular indirect opthalmoscope according to the invention, with casing parts separated to show internal detail.

The ophthalmoscope is of generally inverted T-shape and comprises two casing parts 1, 2 the edges of which are attached together to enclose the major components of the ophthalmoscope. Two spaced brackets 3 (one of which is visible in FIG. 1) project through an aperture in the rear casing part 2, and each bracket has a slot 4 for the passage of a headband (not shown) to encircle the head of the user of the ophthalmoscope. The brackets 3 are rigidly attached to a block 5 on which is mounted a generally cylindrical optics chassis 6 which accommodates a light source, in this case an incandescent lamp (not shown) powered by an electrical cable (also not shown). The light source produces an illumination beam which is directed downwardly onto an illumination mirror 7 which directs the illumination beam through an aperture 8 in the front casing part 1 towards the eye being examined.

The base of the T-shape accommodates the opthalmoscope viewing optics which include a pair of viewing mirrors 9, 10 and left-hand and right-hand eyepieces. The eyepieces 12, 13 are mounted on an optical base plate 14 which is secured in the casing so as to be rigid with the bracket 3, the block 5 and the chassis 6, this rigid assembly forming the opthalmoscope frame on which the various moveable opponents are mounted.

Figure 4:
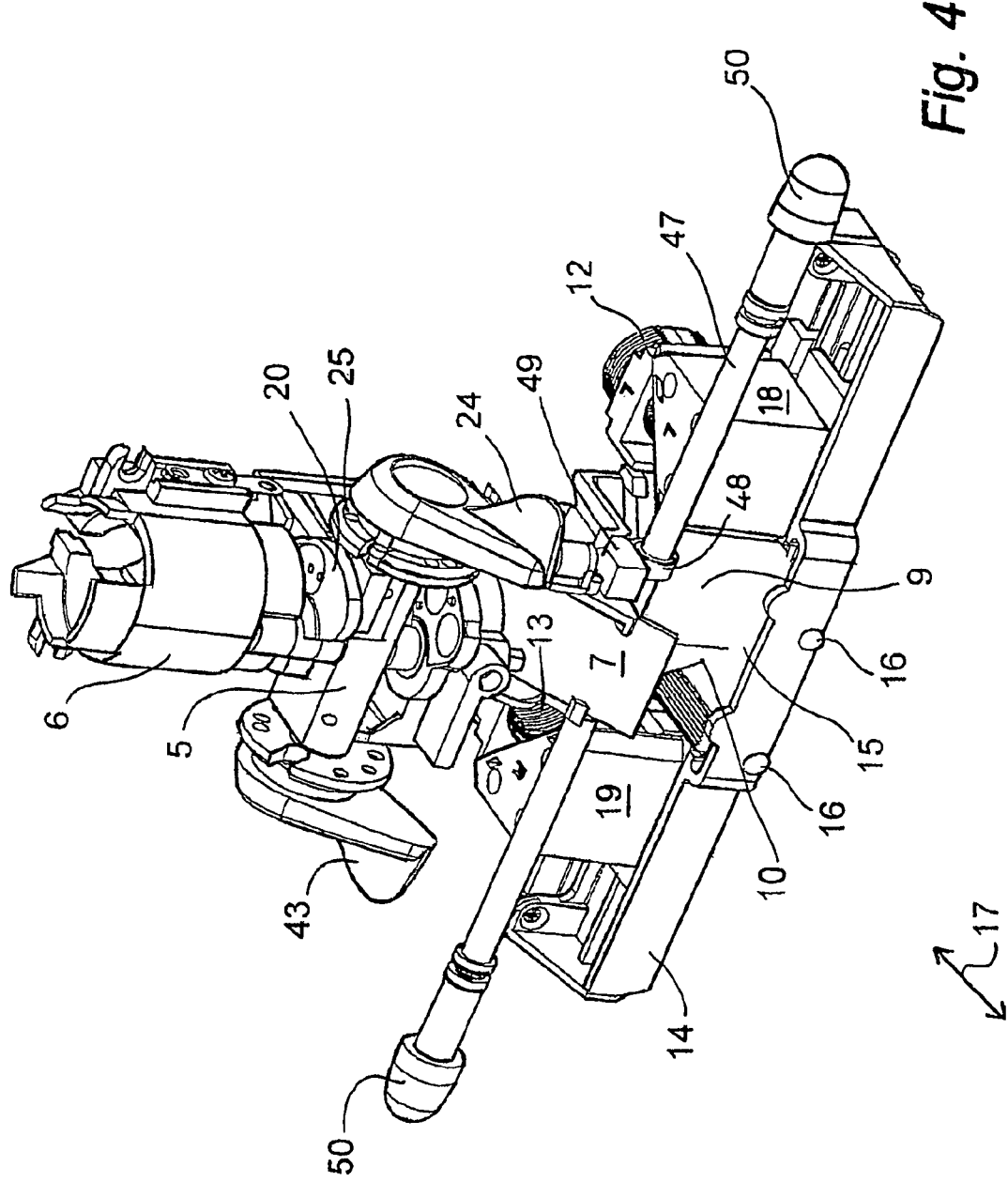
FIG. 4 is a front view of the opthalmoscope with casing parts removed.

The pair of viewing mirrors 9, 10 are rigidly mounted on a carriage 15 which is guided on two rods 16, for limited sliding movement on the base plate 14, in the direction towards or away from the eye being examined, that is in the direction indicated by the arrow 17 in FIGS. 1 and 4.

The pair of viewing mirrors 9, 10 thus act as an optical splitter which directs light travelling along left and right viewing paths to the two eyepieces 12, 13 respectively, the adjustable sliding movement of the splitter altering the lateral separation of the viewing paths.

Figure 2:
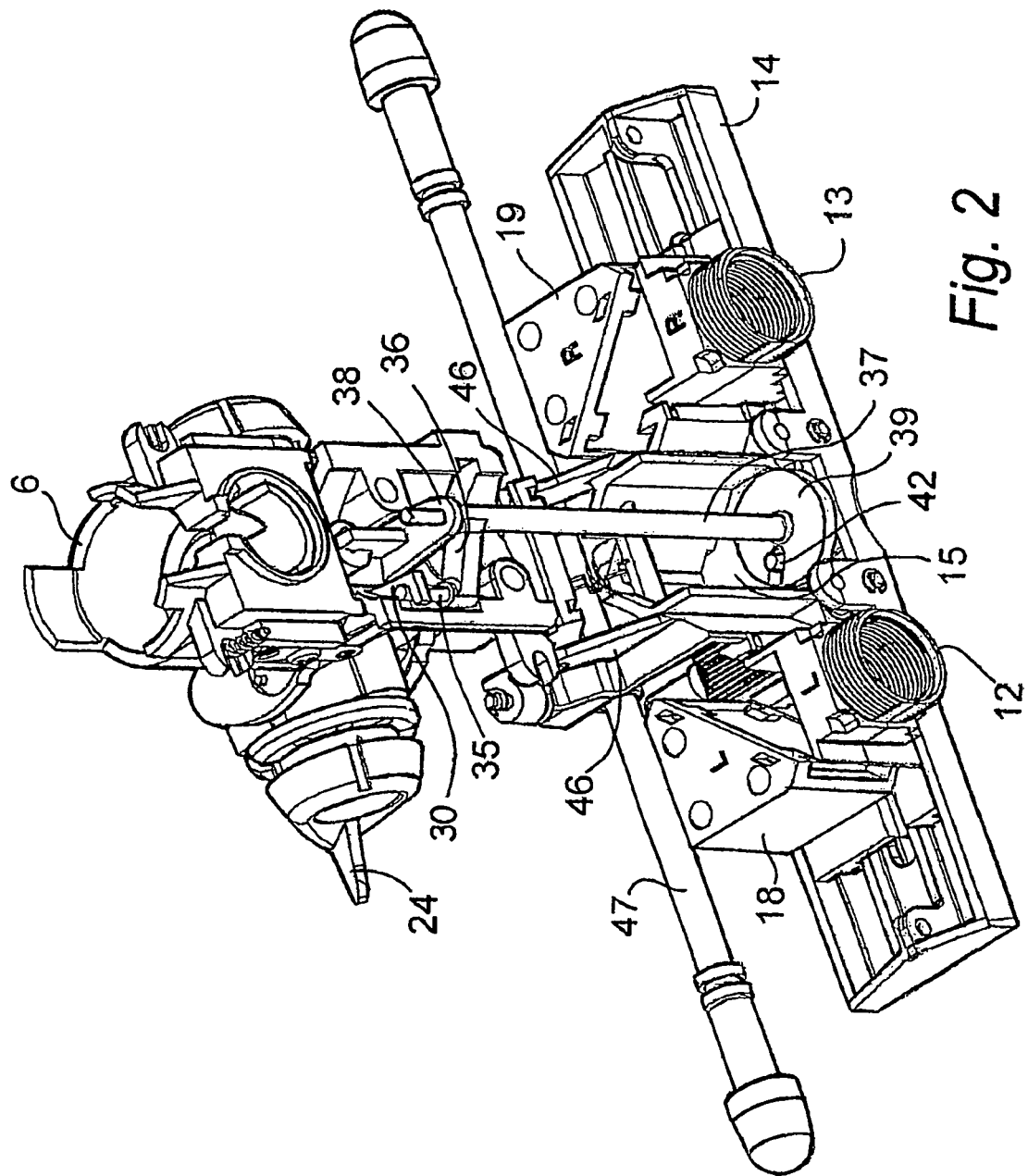
FIG. 2 is a view showing the rear of the opthalmoscope with casing parts removed.

As best seen in FIGS. 2 and 4, the two eyepieces 12, 13 corporate with blocks 18, 19 slideable in the base plate 14 in a horizontal direction towards or away from the viewing mirrors, so that the eyepieces 12, 13 can be clamped in a desired adjusted position.

Reverting to the illumination optics, an aperture holder 20 is pivotally mounted with respect to, and immediately above, the block 5 about a vertical axis defined by a spindle. The aperture holder 20 supports a graticule 22 which has therein a series of spaced holes 23 of differing diameters, a selected one of which can be bought into register with the illumination beam by appropriate rotational positioning of the aperture holder 20. The rotational position of the aperture holder 20 is controlled by a manually rotatable control knob 24 which, together with an index wheel 25, is mounted in the block for rotational movement about a transverse horizontal axis.

Figure 5:
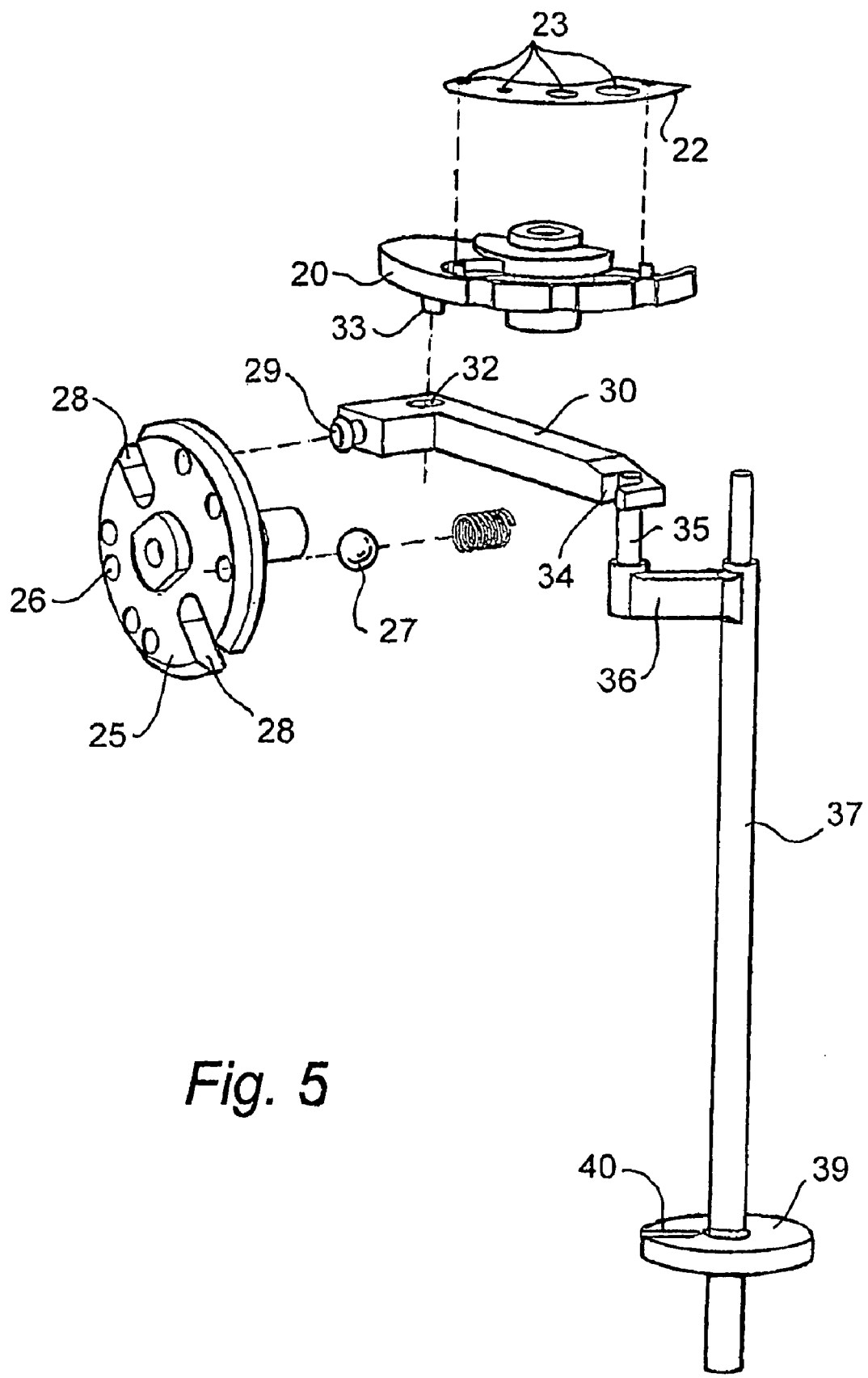
FIG. 5 is an exploded view of parts of a linkage mechanism of the opthalmoscope.

Referring to FIG. 5, the index wheel 25 has a plurality of holes 26 into any one of which a spring loaded ball 27 is urged to impart "feel" to the rotational motion of the knob 24. The index wheel 25 also has two radial slots 28 within one of which slides a pin 29 carried on one end of an elongated link 30 into a hole or recess 32 in which projects a pin 33 extending downwardly from the aperture holder 20. When the control knob 24 is rotated to a new index position, the pin 29 slides in its slot 28, causing the link 30 to move with a complex combined translational and rotational movement, having the effect of moving the pin 33 to cause the aperture holder 20 to rotate about the spindle to bring a graticule of different size into register with the illumination beam.

Figure 3:
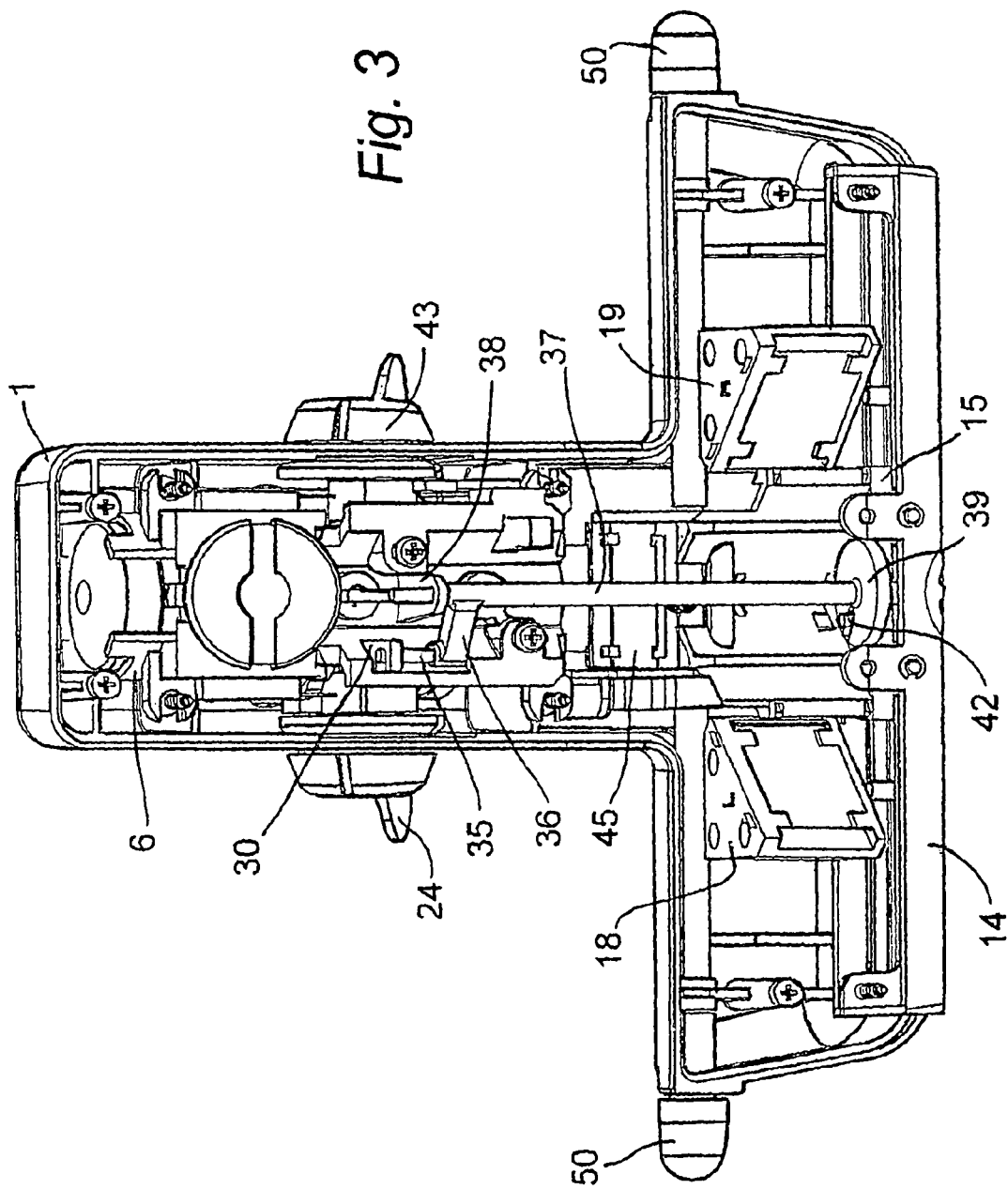
FIG. 3 is another view of the rear of the opthalmoscope with a casing part removed.

Remote from its end carrying the pin 29, the link 30 has a slot 34 into which extends a pin 35 carried on the end of a crank arm 36 mounted near the upper end of a spindle 37 rotatably mounted in the opthalmoscope frame about a vertical axis. The upper end of the spindle 37 is received in a pivot hole in a bracket 38 (FIG. 3) projecting from the frame, and the lower end of the spindle 37 is pivotably received in a sylindrical hold formed in the base plate 14. A short distance above this pivotable support of the spindle 37, the latter has attached thereto a disc-like flange 39 having a radial slot 40 which received a pin 42 (FIGS. 2 and 3) carried by the carriage 15. When the link 30 moves to rotate the aperture holder 20, the link 30 also moves the pin 35 to rotate the crank 36, which in turn rotates the spindle 37. This causes the pin 42 to move within the slot 40 in the flange 39 to cause a corresponding translational movement to be imparted to the carriage 15.

On the other side of the casing from the control knob 24, the opthalmoscope carries a similar knob 43, the function of which is to drive a further index wheel 44 which rotates a filter holder carrying a plurality of different coloured filters, a selected one of which can be brought into register with the illumination beam by appropriate rotation of the control knob 43.

The illumination mirror 7 is attached to a underlying mirror mount 45 pivotally mounted on the carriage 15 about a horizontal transverse axis. For this purpose, the carriage 15 has a pair of upwardly extending brackets 46 having horizontally aligned pivot holes into which project pivot pins extending outwardly from the mirror mount 45. The rotational position of the illumination mirror 7 is controlled by a spindle 47 which is pivotally mounted in the carriage 15 and, at an intermediate position along its length, carries a cam 48 onto which is urged by a spring a cam follower 49 the upper surface of which engages a pin projecting from the mirror mount 45. The end of the spindle carries knobs 50 for ease of manual rotation of the spindle 47, an adjustment which rotates the cam 48 and displaces the cam follower 49 to cause alteration in the angular position of the illumination mirror 7 with respect to the carriage 15. It will be appreciated that sliding movement of the carriage 15 with respect to the opthalmoscope frame alters the height of the illumination beam but does not itself alter the angle of the illumination mirror with respect to the carriage.

To examine an eye, the user dons the opthalmoscope, using the headband. Apart from selection of the desired colour filter by the control knob 43, the only adjustment necessary is by way of the control knob 24 which not only adjusts the size of the illumination beam by moving the aperture holder 20, but also causes a corresponding adjustment in the position of the carriage 15 which simultaneously adjusts the position of the viewing mirrors 9, 10 so as to alter the lateral separation of the viewing paths and alters the position of the illumination mirror 7 so as to alter the height the illumination beam directed towards the hand-held condensing lens and, from there, to the eye. Normally, the user will commence with the widest illumination beam but if the pupil of the eye cannot accommodate such a wide illumination beam the user can, by rotating the control knob 24, reduce the size of the illumination beam and, at the same time, adjust the position of the viewing mirrors 9, 10 and the illumination mirror 7 without the need to make any other adjustment, because the provision of the mechanical linkage between the aperture holder 20 and the carriage 15 ensures that any adjustment in the position of the aperture holder 20 automatically results in adjustment of the position of the carriage 15 on which are mounted the viewing optics and illumination mirror. If the size of the illumination beam is increased, the carriage 15 is moved towards the eye and if the size of the illumination beam is decreased the carriage 15 is moved away from the eye. If the angular position of the illumination mirror 7 then needs adjustment, this can be effected by manual rotation of the spindle 47.

The invention claimed is:

1. A binocular indirect ophthalmoscope comprising illumination optics including an adjustment device for selectively altering the size of an illumination beam and a beam directing device for directing the illumination beam of selected size to an eye to be viewed, the ophthalmoscope further comprising viewing optics including left hand and right hand viewing eyepieces, an optical splitter for directing light travelling along left and right viewing paths respectively to the two eyepieces, wherein the beam directing device and optical splitter are moveable with respect to a frame of the ophthalmoscope respectively to alter the position of the illumination beam and the lateral separation of the viewing paths, characterised in that the adjustment device for selectively altering the size of the illumination beam, the optical splitter and the beam directing device are linked such that adjustment of the size of the illumination beam results in a corresponding adjustment in the beam directing device and the position of the optical splitter.

2. An ophthalmoscope according to claim 1, wherein the beam directing device comprises an illumination mirror, the optical splitter and the illumination mirror being mounted on a common carriage moveable with respect to the frame of the ophthalmoscope in a direction towards and away from the eye.

3. An ophthalmoscope according to claim 2, wherein an enlargement in size of the illumination beam causes the carriage to move in a direction towards the eye to be viewed and a reduction of the size of the illumination beam causes the carriage to move in a direction away from the eye to be viewed.

4. An ophthalmoscope according to claim 1, wherein the link between the adjustment device, the optical splitter and the beam directing device is provided by a mechanical linkage.

5. An ophthalmoscope according to claim 4, wherein the mechanical linkage includes a spindle rotatably mounted in the frame, the spindle extending between an upper region of the ophthalmoscope, where the adjustment device is located, and a lower region of the ophthalmoscope where the carriage is located.

6. An ophthalmoscope according to claim 5, wherein the linkage includes a link which transmits adjusting motion from the device to a crank projecting from the upper end of the spindle.

7. An ophthalmoscope according to claim 1, wherein the adjustment device comprises an aperture holder moveable with respect to the frame in order to bring apertures of different size into alignment with the illumination beam in order to alter the size of the illumination beam reaching the illumination mirror, and a manually rotatable member for moving the aperture holder between indexed positions thereof.

8. An ophthalmoscope according to claim 1, wherein the angular position of the illumination mirror with respect to the carriage is adjustable about a horizontal axis parallel to the two light components emerging from the optical splitters, so that the angle of the illumination beam in a vertical plane is adjustable independently of the prevailing position of the carriage.

9. A binocular indirect ophthalmoscope comprising a frame; a light source supported by the frame for producing an illumination beam; an adjustment device including an aperture holder moveable with respect to the frame for altering the size of the illumination beam and a manually operable control member for controlling movement of the aperture holder; an illumination mirror for directing the illumination beam of adjusted size to an eye to be viewed; viewing optics including left-hand and right-hand viewing eyepieces and an optical splitter for directing light travelling along left-hand and right-hand viewing paths respectively to the two eyepieces; and a carriage moveable with respect to the frame in a direction towards and away from the eye to be examined, wherein the illumination mirror and the optical splitter are mounted on the carriage and the adjustment device is linked to the carriage such that movement of the control member in a direction causing reduction in the size of the illumination beam necessarily causes movement of the carriage, and therefore of the illumination mirror and the beam splitter, in a direction away from the eye to be viewed, and movement of the control member in a direction causing enlargement of the size of the illumination beam necessarily causes movement of the carriage, and therefore of the illumination mirror and the beam splitter, in a direction towards the eye to be viewed.

10. An ophthalmoscope according to claim 9, wherein the aperture holder is rotatable, with respect to the frame, to alter the size of the illumination beam, and wherein the link between the aperture holder and carriage is provided by a mechanical linkage which is operable to couple said rotational movement of the aperture holder to the movement to the carriage, the movement of the carriage being translational movement with respect to the frame.

11. A binocular indirect ophthalmoscope comprising illumination optics including an adjustment device for selectively altering the size of an illumination beam and a beam directing device for directing the illumination beam of selected size to an eye to be viewed, the ophthalmoscope further comprising viewing optics including left hand and right hand viewing eyepieces, an optical splitter for directing light travelling along left and right viewing paths respectively to the two eyepieces, wherein the beam directing device and optical splitter are moveable with respect to a frame of the ophthalmoscope respectively to alter the position of the illumination beam and the lateral separation of the viewing paths, in which the adjustment device, the optical splitter and the beam directing device are linked such that adjustment of the size of the illumination beam results in a corresponding adjustment in the beam directing device and the position of the optical splitter, the link between the adjustment device, the optical splitter and the beam directing device being provided by a mechanical linkage including a spindle rotatably mounted in the frame, the spindle extending between an upper region of the ophthalmoscope, where the adjustment device is located, and a lower region of the ophthalmoscope where the carriage is located.

12. An ophthalmoscope according to claim 11, wherein the linkage includes a link which transmits adjusting motion from the device to a crank projecting from the upper end of the spindle.

13. An ophthalmoscope according to claim 11, wherein the beam directing device comprises an illumination mirror, the optical splitter and the illumination mirror being mounted on a common carriage moveable with respect to the frame of the ophthalmoscope in a direction towards and away from the eye.

14. An ophthalmoscope according to claim 13, wherein an enlargement in size of the illumination beam causes the carriage to move in a direction towards the eye to be viewed and a reduction of the size of the illumination beam causes the carriage to move in a direction away from the eye to be viewed.

15. An ophthalmoscope according to claim 13, wherein the adjustment device comprises an aperture holder moveable with respect to the frame in order to bring apertures of different size into alignment with the illumination beam in order to alter the size of the illumination beam reaching the illumination mirror, and a manually rotatable member for moving the aperture holder between indexed positions thereof.

16. An ophthalmoscope according to claim 13, wherein the angular position of the illumination mirror with respect to the carriage is adjustable about a horizontal axis parallel to the two light components emerging from the optical splitters, so that the angle of the illumination beam in a vertical plane is adjustable independently of the prevailing position of the carriage.

* * * * *